(12) United States Patent
Harada et al.

(10) Patent No.: US 7,189,677 B2
(45) Date of Patent: Mar. 13, 2007

(54) RICE SEED COATED WITH AN AGRICULTURE CHEMICAL

(75) Inventors: Naoki Harada, Saitama (JP); Noriko Maeda, Saitama (JP)

(73) Assignee: Incotec Japan Co., Ltd., Saitama (JP)

( * ) Notice: Subject to any disclaimer, the term of this patent is extended or adjusted under 35 U.S.C. 154(b) by 699 days.

(21) Appl. No.: 10/258,327

(22) PCT Filed: Apr. 18, 2001

(86) PCT No.: PCT/JP01/03314

§ 371 (c)(1),
(2), (4) Date: Dec. 17, 2002

(87) PCT Pub. No.: WO01/78507

PCT Pub. Date: Oct. 25, 2001

(65) Prior Publication Data

US 2004/0025208 A1    Feb. 5, 2004

(30) Foreign Application Priority Data

Apr. 18, 2000    (JP)    .............................. 2000-116592

(51) Int. Cl.
*A01N 25/26*    (2006.01)
*A01P 3/00*    (2006.01)
*A01P 7/04*    (2006.01)
*A01P 1/00*    (2006.01)

(52) U.S. Cl. .................. 504/100; 47/58.1 SE; 47/57.6; 47/DIG. 9; 424/417; 424/419

(58) Field of Classification Search ................ 504/100; 47/57.6, 58.1 SE, DIG. 9
See application file for complete search history.

(56) References Cited

U.S. PATENT DOCUMENTS 5,876,739 A    3/1999    Turnblad et al.
6,261,996 B1    7/2001    Klittich et al.

FOREIGN PATENT DOCUMENTS

AU    716873    12/1996
JP    2866921 B2    3/1999

*Primary Examiner*—Sreeni Padmanabhan
*Assistant Examiner*—Renée Claytor
(74) *Attorney, Agent, or Firm*—Day Pitney LLP

(57) ABSTRACT

The invention provides a rice seed coated with an agricultural chemical, characterized in that a rice seed is deprived of husk and the surface of said rice seed is coated with a binder containing an agricultural chemical. The rice seed is suitable to be germinated by maintaining the seed for at least three days at 20 to 40 degrees C.

12 Claims, No Drawings

RICE SEED COATED WITH AN AGRICULTURE CHEMICAL

FIELD OF THE INVENTION

This invention relates to rice seeds coated with an agricultural chemical.

BACKGROUND OF THE INVENTION

In order to protect rice seeds or seedling from diseases caused by fungi or bacteria, intact rice seeds in the husk are conventionally soaked in a solution of one or more fungicidal and/or bactericidal agents before sowed. However, this process can not fully prevent diseases caused by fungi or bacteria. Moreover, this process has a pollution problem caused by discharge of the solution of the fungicidal and/or bactericidal agent after seed soaking as well as an economical problem by loss of the fungicidal or bactericidal agent. Furthermore, in order to completely prevent damage caused by the fungi after sowing, the fungicidal agent is needed to be applied again after sowing. Also in order to prevent damage by insects after sowing, the sprinkling of the insecticidal agent is needed.

Coating intact rice seeds with a fungicidal or bactericidal agent was performed for the purpose of solving the above-mentioned problems. However, this could not sufficiently solve the problems.

Beside, in order to germinate intact rice seeds, it is necessary to have the seeds first absorb enough water. Thus, intact rice seeds need to be kept under water for a considerable time period to absorb enough water through the husk before sowing so as to attain uniform sprouting, because the outside of the seeds is covered by the husk.

In the conventional technology, intact rice seeds with husk are coated, on the husk, with a binder which contains an agricultural chemical, and are soaked in water containing one or more fungicidal or bactericidal agents for about one day to sterilize adhering fungi or bacteria. Subsequently, the water containing the fungicidal or bactericidal agents is replaced with fresh water. Then, one waits for development of the sprout of rice seeds, while circulating optionally heated water through the mass of rice seeds.

Rice seeds usually start sprouting and developing the coleoptile of the embryo in about three days after the start of circulation of water, and come into a so-called "pigeon breast" state. The rice seeds in the pigeon breast state are sown on soil in a tray, and reared in a dark place for three to seven days. Although radicles come out in this period of time, the leave which have first been developed grow further, so that the seedlings have much better developed leaves, compared to the development of the radicles.

Then the rice seeds in this developed state of sprout growth are moved together with the tray from the dark place to a place with light such as a greenhouse and allowed to grow according to the conventional method.

However, in this method, a considerable time of soaking in water is required before sprouting; the sprouted rice seeds generally show non-uniform growth and tend to fall sick; and furthermore, the water containing the fungicidal or bactericidal agent used in the sprouting process is discarded to cause a pollution problem and a loss of the fungicidal or bactericidal agent.

In addition, the radicles which just came out of the rice seeds in this method are comparatively weak to chemical toxicity of an insecticidal agent. If an insecticidal agent is used when the radicles are still small, growth of the radicles is arrested by the toxicity so that growth of rice seedlings is slow. Accordingly, an insecticidal agent can be used only after considerable development of the radicles. Then, the sprouted rice might be eaten by insects.

SUMMARY OF THE INVENTION

The present invention provides a rice seed coated with an agricultural chemical which rice seed is almost completely protected from diseases and insects, can rapidly attain almost uniform and good sprout and can grow into healthy seedling.

The present inventors have made investigation to find out the reasons for the above-mentioned various problems. The inventors have found that immersion of rice seeds in water in a considerable time till development of a sprout is necessary for sufficient absorption of water into the seeds through the husk in order to make the sprouting as uniform as possible; however, if the soaking time is too long, the work efficiency is bad and, on the other hand, if the soaking time is too short, the absorption of water is not uniform and the sprouting is not uniform among the seeds; meanwhile, if the husk is removed from seeds, soaking in water is unnecessary, but mold will grow intensely during sprouting to cause death of more than 50% of the seeds during the sprouting; and further, if radicles are made to first emerge before coleoptile do, the radicles are more resistant to an insecticidal agent than in a conventional method, the insecticidal agent can be applied by simultaneous coating together with a fungicidal or bactericidal agent, and then the insecticidal agent can start exhibit its effects immediately after sprouting.

Based on these pieces of knowledge, the inventors have made the following invention. Thus, the invention is a rice seed coated with an agricultural chemical, characterized in that a rice seed is deprived of husk and the surface of said rice seed is coated with a binder containing an agricultural chemical.

Japanese Patent No. 2,866,921 discloses non-diseased brown rice seeds with an artificial coat, characterized in that rice seeds are de-husked to remove the husk in which infectious fungi or bacteria might lie, washed with water to obtain almost sterile brown rice, which are then coated, without being disinfected by agricultural chemicals, on the surface with an artificial coat. It is essential in that patent that de-husked rice seeds are washed with water to prevent germs attached to the husk from contaminating the brown rice seeds and that the de-husked rice seeds are not sterilized with an agricultural chemical in order to reduce the amount of agricultural chemicals to be used as much as possible. Meanwhile in the present invention, it is not essential that de-husked rice seeds are washed or soaked. The surface of the de-husked brown rice seeds are covered with an agricultural chemical. Since the surface of the brown rice seeds is disinfected by an agricultural chemical covering the surface of the rice seeds, washing after removing the husk becomes unnecessary.

In the above-mentioned patented invention, disease germs present in or on the husk are removed because the husk is removed from the seed. However, disease germs infectious to rice seeds exist not only in husk but in soil, water, air, etc. Therefore, it is necessary to cope with the disease germs after sowed in soil in a conventional manner which is previously practiced. Meanwhile in the present invention, the surface of the de-husked rice seeds is covered with an agricultural chemical and, therefore, all of disease germs present in or on the husk, and disease germs present in soil, water, air, etc. can be coped with.

Therefore, unlike the above-mentioned patented invention, the present invention has an advantage that no further treatment for coping with a disease germ is necessary. As a result, even though the de-husked rice seeds are covered with agricultural chemicals, the total amount of the agricultural chemicals used is less.

Preferred Embodiments of the Invention

In a preferred embodiment, the rice seed after de-husked is not washed.

In another embodiment, the rice seed is selected from the group consisting of Oryza sativa sp. japonica, Oryza sativa sp. javanica, Oryza sativa sp. indica, and hybrids thereof In another embodiment, the agricultural chemical is selected from the group consisting of fungicidal agents, bactericidal agents and insecticidal agents.

In another embodiment, the fungicidal or bactericidal agent is applied in an amount of 0.1 to 10 g per kg of the de-husked rice.

In another embodiment, the insecticidal agent is applied in an amount of 3 to 20 g per kg of the de-husked rice.

In another embodiment, the fungicide is selected from the group consisting of phenylpyrrole fungicides, azole fungicides, and strobilurine fungicides.

In another embodiment, the insecticide is selected from the group consisting of neo-nicotinide insecticides, carbazates insecticides, pyrethroid ether insecticides, and pyridine azomethine insecticides.

In another embodiment, the binder is selected from the group consisting of polyvinyl acetates, polyvinyl alcohols, and polyvinyl pyrrolidones.

In another embodiment, the binder is a mixture of 0 to 50% by weight of polyurethane and 100 to 50% by weight of polyvinyl alcohol.

In another embodiment, the rice seed is to be germinated by keeping the seed under aerobic conditions which lead to emergence of a radicle first before emergence of a coleoptile.

In another embodiment, the rice seed is to be germinated by maintaining the seed for at least three days at 20 to 40 degrees C.

In another embodiment, the rice seed is to be germinated by maintaining the seed for 4 to 9 days at 25 to 35 degrees C.

In another embodiment, the rice seed is to be germinated by maintaining the seed for 4 to 9 days around 30 degrees C.

The invention also provides a method of germinating the seeds as described above, wherein the seeds are kept in aerobic conditions which lead to emergence of a radicle first, before emergence of a coleoptile.

Any rice may be used, but is preferably selected from the group consisting of Oryza sativa sp. japonica, Oryza sativa sp. javanica, Oryza sativa sp indica, and hybrids thereof.

There is no particular limitation on a method of removing husk from rice seeds in the invention, as long as rice seeds are not broken or greatly impaired. Any known method may be used. For example, twin rolls are used to remove husk. More specifically, for example, intact rice seeds are passed between twin rolls with a predetermined gap between the rolls, one of which rolls has a rotation speed and a rotation direction different from those of the other roll. Then, suitable friction takes place between the twin rolls and the intact rice seeds to remove the husk from the rice seeds. If husk is not completely removed from the rice seeds by the above-mentioned operation, the rice seeds are again passed between twin rolls. The rotation speed and the gap of the twin rolls here may be the same as or different from those of the first pass. The rotation speeds and gaps may be suitably determined by those having ordinary skill.

Commercially available twin rolls can be used such as, for instance, MP, MPS and MPC series, such as MPS50, MP50, MP40, MPC40 and MPC35 (trademarks, ex Iseki & Co., Ltd.), LTA series such as LTA10, LTA15, LTA20 and LTA30 (trademarks, ex Iseki & Co., Ltd.), MX series such as M-300 Pearlmate (trademark, ex Iseki & Co., Ltd.), 5HP series such as SY3700D, SY3700DC and NR3700SD (trademarks, ex Yammar Diesel Engine, Inc.), and HT10PP, HR10PN, HR10N and THU35A (trademarks, ex Satake, Inc.).

The de-husked rice seeds show rapid and uniform absorption of water and can germinate in a relatively wide range of temperature, compared to intact rice seeds with husk. The brown rice seeds with no husk are preferably stored at a temperature of 15 to 25 degrees C. in air with a relative humidity of 30 to 40%, before and after coated with the binder containing an agricultural chemical.

As the agricultural chemicals, use may be made of fungicidal and bactericidal agents, insecticidal agents, biocides, disinfectants and biological organisms beneficial to control pathogens, preferably fungicidal or bactericidal agents, and insecticidal agents. Any known fungicidal or bactericidal agents and insecticidal agents may be.

Examples of the fungicidal or bactericidal agents may include phenylpyrrole fungicides, such as fenpiclonil and fludioxonil, azole fungicides such as triflumizol, propiconazole and tebuconazole, and strobilurine fungicides such as azoxystrobin. Those commercially available include Rovral (trademark, ex Rhone-Poulenc), Ridomyl MZ (trademark, ex Novartis Agro), Healthied (trademark, ex Kube), Trifmine WP (trademark, ex Nissan Chemical Industries, Ltd.), Homai and Homaicoat (trademarks, ex Nippon Soda Co., Ltd.), Benlate-T and Benlate 50 WP (trademark, ex Du Pont); Thionock 50, Daconil, Kes, Spaglin, Dacolate and Orthocide (trademarks); and Savior (trademark, ex Novartis Agro). More preferably used are Rovral, Ridomyl MZ, Healthied, Trifmine WP and Savior.

The insecticidal agent include neo-nicotinide insecticides such as imidacloprid, acetamiprid and thiametoxam, carbazates insecticides such as bifenazate, pyrethroid ether insecticides such as etofenprox and flufenprox, and pyridine azomethine insecticides such as pymetrozine. Commercially available products include Mospilan (trademark, ex Nippon Soda Co., Ltd.), Actara and Cruiser (trademarks, ex Novartis Agro), Trebon (trademark, ex Mitsui Chemical), Gaucho, Admire, Confidor and Provado (trademarks, ex Nihon Bayer), Best Guard (TI-435) (trademark, ex Takeda Chemical Industries, Ltd.), and AKD-1022 (trademark, ex Agro-Kanesho). Baidit2, Baidit3 and Padan WS (trademarks) may also be used.

The biocides include Acticide 45, Acticide CSP, and Acticide EW (trademarks, ex Thor Industries), for which more information is available at www.thor-chemicals.com. The disinfectants include alcohols, sodium hypochlorite, and potassium or sodium triphosphate. The biological organisms beneficial to control pathogens include Trichoderma harzianum, Bacillus subtillus, and Gliocladium virens, for which more information is available at www.bioworksbiocontrol.com.

The quantity of the fungicidal or bactericidal agent and the quantity of the insecticidal agent to be applied depend on a type of those agents. The fungicidal or bactericidal agent is applied to the rice seed surface preferably in a ratio of 0.1 to 10 grams, more preferably 0.5 to 2 grams, per kilogram of the brown rice seeds from which husk has been removed. The insecticidal agent is applied to the rice seed surface preferably in a ratio of 3 to 20 grams, more preferably 5 to 10 grams, per kilogram of the brown rice seeds from which husk has been removed. When the fungicidal or bactericidal agent and the insecticidal agent which are preferably of slow release or lag-burst release are used in the above-mentioned ranges, the effects are maintainable over 2 to 4 months after sowing. Conventionally, a period of continuous effectiveness is about 2 weeks for usual fungicidal or bactericidal agents, or 2 to 4 months for special fungicidal or bactericidal agents; and about 2 months for insecticidal agents. According to the present invention, a period of the continuous effectiveness is generally prolonged, compared to the above-mentioned conventional manner.

The biocide and the disinfectant are each applied to the de-husked rice seed surface preferably in a ratio of 0.1 to 10 grams, more preferably 0.5 to 2 grams, per kilogram of the brown rice seeds from which husk has been removed. The amount of the biological organism beneficial to control pathogens is preferably $1 \times 10^7$ to $1 \times 10^{10}$ CFU, more preferably $5 \times 10^8$ to $5 \times 10^9$ CFU, per kilogram of the brown rice seeds from which husk has been removed. Here, "CFU" or colony forming unit is a biable count of the organism in question when the organism is cultured on an agar medium in a petri-dish.

In addition to the above-mentioned fungicidal or bactericidal agent and the insecticidal agent, the surface of the brown rice seed of this invention may be provided with other substances such as, for example, rodent killing agents, weed killers, attracting agents, repellent agents, plant growth regulators such as giberillic acid, auxine and citokinine, nutrients such as potassium nitrate, magnesium sulphate, and iron gelate, plant hormones, pigments, fillers, wax, oxidizing or anti-oxidation agents, activated carbon, surface-active agents, spreaders, gene activators such as BRX-156 (ex Biorex), systemic resistance activators such as Bion (Acebenzolar-S-methyl, ex Novartis Agro), and Messenger (Harpin protein, ex Cornel University, Eden Bioscience), plant growth promotors such as Grow Ace (fungi extract, ex Snowbrand), and Tachigare (NEB-glycoside, ex Sankyo Chemical), and others including chitosan (chitin-based polymer), seed weed extracts, plant extracts, and minerals.

A binder is used to bind the above-mentioned fungicidal or bactericidal agent and the insecticidal agent onto the brown rice seed from which husk has been removed. Any known binder can be used. If water is used as a solvent, use is preferably made of water-soluble binders, or water-emulsifiable or -dispersible binders. Examples of the binders include polyvinyl acetate, polyvinyl alcohol, carboxy methyl cellulose, methyl cellulose, hydroxypropyl methyl cellulose, hydroxyethyl cellulose, cellulose polymer, chitin, polyvinylidene chloride, water-dispersible polyacrylic resins, polysodium acrylate, polyacrylamide, acrylate copolymers, polyvinyl pyrrolidone, polyurethane, polysaccharides, starch, and gum type binders. Preferred are polyvinyl acetate, polyvinyl alcohol, polyvinyl pyrrolidone, water-dispersible polyacrylic resins, and polyurethane. These binders may be used alone or in combination of two or more of these.

The fungicidal or bactericidal agent and the insecticidal agent confined in the binder come to exhibit their effects gradually on account of the binder, so that the effects are maintained for a prolonged period. It is possible to combine a plurality of the binders, such as polyvinyl alcohol and polyurethane. A release rate of the fungicidal or bactericidal agent and the insecticidal agent can preferably be controlled, using a binder mixture comprising 0 to 50% by weight of polyurethane and 100 to 50% by weight of polyvinyl alcohol.

Although the amount of the binder to be applied to the rice seed surface depends somewhat upon the kind of the binder, it may be 0.3 to 30 g, usually 0.5 to 10 g, more preferably 1 to 6 g, per kg of the brown rice seeds from which husk has been removed. For example, 1 kg of the brown rice seeds from which husk has been removed is provided preferably with 1 to 20 g, more preferably 2 to 10 g, most preferably 3 to 6 g, of polyvinyl acetate; 0.3 to 20 g, more preferably 0.5 to 4 g, most preferably 1 to 2 g, of polyvinyl alcohol; 0.5 to 14 g, more preferably 1 to 7 g, most preferably 2 to 4 g, of hydroxypropyl methyl cellulose; or 0.5 to 12 g, more preferably 1 to 6 g, most preferably 1.5 to 3 g, of polyvinyl pyrrolidone. Below the aforesaid lower limits, it is difficult to provide the brown rice seeds with the required amounts of the fungicidal or bactericidal agent and the insecticidal agent in good conditions.

In this invention, a method of coating the surface of the de-husked brown rice seeds with the fungicidal or bactericidal agent and/or the insecticidal agent is not particularly limited, and any known method can be used. For instance, the fungicidal or bactericidal agent and/or the insecticidal agent and the binder are dissolved, emulsified or dispersed in a solvent, preferably water, to obtain a solution, emulsion or dispersion, which is then sprayed on the de-husked brown rice seeds or in which the de-husked brown rice seeds are soaked. The spraying is preferred. As a spray-coating equipment, use may be made of rotation granulator type coating machines, such as type 9300.00.00, 9310.00.00, 9320.00.00, and 9330.00.00, ex Seed Processing Holland; Satec Concept 3.10, ex Cimbria Heid GmbH, Austria; Centricoater CC20, ex Willy Niklas, Germany; and W.N.5/500, ex Gustaphson, U.S.A.

Subsequently, the rice seeds coated with the fungicidal or bactericidal agent and/or the insecticidal agent as mentioned above are dried. In order to maintain the good quality of the coated rice seeds, the seeds are preferably dried in air preferably at 30 to 50 degrees C., preferably until they reach an equilibrium at a relative humidity of 30 to 40%.

The agricultural chemical-coated rice seeds of the invention thus obtained are then sowed on soil in a tray which may be such currently used for the sprouting of usual rice seeds, and are maintained under the following conditions for sprouting.

In the invention, the rice seeds covered with the agricultural chemicals are germinated in aerobic conditions where radicles will emerge before coleoptiles emerge. The aerobic conditions herein mean that an oxygen concentration in the atmosphere near the surface of the coating on the rice seeds is preferably at least 1.0% by volume, more preferably at least 3.0% by volume, further preferably at least 5.0% by volume. When the rice seed is covered with soil, the oxygen concentration refers similarly to that of the atmosphere near the surface of the coating, but oxygen contained in the soil is not taken into consideration. If sprouting is carried out in an anaerobic atmosphere with an oxygen concentration less than the above-mentioned lower limit, for example, in underwater conditions as previous where the oxygen concentration is about 5 to 15 p.p.m. at atmospheric pressure at 20 to 30 degrees C., development of coleoptiles from the seed is much remarkable, compared to development of radicles, and the growth is not uniform among seeds, which is undesirable.

In the case of the rice seed of this invention covered with the fungicidal or bactericidal agent and/or the insecticidal agent, if an atmosphere near the surface of the coating on the seeds is maintained in aerobic conditions, the inside of the coating, i.e., the surface of the de-husked rice is also held in aerobic conditions. Therefore, development of radicles is rapid and remarkable, without non-uniformity in sprouting, much more than development of coleoptiles, and seedlings grow well and healthily.

The above-mentioned aerobic conditions are maintained preferably at 20 to 40 degrees C., more preferably 25 to 35 degrees C., particularly preferably 30 to 35 degrees C. usually for a period of from a time when the rice seed is sowed on soil to a time when it germs via embryogenesis, preferably for at least 3 days, more preferably 4 to 9 days, whereby sprouting of the rice seeds can be promoted and can be made more uniform.

The rice seeds after sowed can be preferably covered with vermiculite. It is possible to conduct usual agricultural-chemicals processing on the soil after the sowing. Such a degree of sprinkling of water after the sowing that the soil remains humid is enough. Irrigation water after the sowing is applied to such extent that the soil remains sufficiently humid. If excessive water is applied or the seeds are submerged under water, it is difficult to maintain aerobic conditions, and anaerobic conditions take place easily, which should be avoided. According to the invention, it is not necessary to store the rice seeds in a dark place, unlike conventional intact rice seeds covered with agricultural chemicals, and then can be put under day lights to germinate.

The rice seeds thus sprouted are cultivated and brought up according to a usual manner.

The present invention provides a rice seed coated with an agricultural chemical which rice seed is almost completely protected from diseases and insects, can rapidly attain almost uniform and good sprout and can grow into healthy seedling. The present rice seed does not require soaking in water containing a bactericide or fungicide, which soaking is needed for germinating conventional rice seeds coated with an agricultural chemical. Therefore, there is no pollution problem or economical problem caused by discarding the water containing an agricultural chemical. It is unnecessary to circulate water during germination any more. Labor of keeping seeds in a dark place for a predetermined time period after germination is unnecessary at all. Radicles which come out prior to coleoptiles are resistant to phyto-toxicity of insecticides and, therefore, even if seeds are covered with an insecticide together with a bactericide, growth of the radicles is not hindered, unlike in the conventional case. In the present seeds, absorption of water can be controlled by the coating and uniform water content is maintained.

Further, an oxygen concentration on the surface on the de-husked seeds can be properly adjusted by the coating, and oxidation of the seeds during storage can be avoided. In addition, the present rice seeds are de-husked and, therefore, are not an object to import restriction, so that one may de-husk rice in a foreign country which is then imported and give the coating in a home country, or one may de-husk rice and give the coating in a foreign country, which is then imported. Thus, one may have more choices on kinds of rice seeds and can prepare seeds with less costs.

In large scale of rice production, rice seeds are sown in paddy fields by an airplane. In order to avoid that the sown seeds float on the water surface and float about by wind or water currents, the seeds are made to adsorb sufficient water in advance. Job of this adsorption requires a lot of time and labor. The present rice seeds do not float in water. In addition, they are smaller and lighter than intact seeds, so that an airplane can carry a larger amount of the seeds for more efficient sowing job. Thus, the present rice seeds are suitable to be air-sown.

The invention will be explained below in more detail with reference to the Examples which shall not be construed to limit the invention.

CONTROL EXAMPLE 1

Intact rice seeds, KOSHIHIKARI, were processed by twin rolls, MX-300 Pearlmate, (trademark, ex Iseki & Co., Ltd.) to remove the husk.

Subsequently, coating liquid A as indicated in the following Table 1 was sprayed on the de-husked rice seeds at room temperature without washing the de-husked rice seeds with water or others, and dried to obtain the de-husked rice seeds coated with a polyvinyl acetate binder. A rotor-granulator type coating machine, model 9320.00.00(ex Seed Processing Holland) was used in the spraying, and the drying was carried out in a relative humidity of 30% in an air flow of a temperature of 30 to 40 degrees C.

The amount of coating liquid A used was 40 g per kg of the de-husked rice seeds. The quantity of the polyvinyl acetate binder applied to the surface of the de-husked rice seeds was 4.8 g per kg of the de-husked rice seeds.

TABLE 1

| Coating Liquid A | |
|---|---|
| Component | Content, % by weight |
| Polyvinyl acetate (binder) | 12.0 |
| Water | 88.0 |

Each 100 grains of the intact rice seeds, the de-husked rice seeds and the de-husked rice seeds processed with coating liquid A were each sown on filter paper (ex Schleicher & Schuel) folded into 50 folds in a plastic container and wetted with 60 cc of water. Under this aerobic condition, they were kept in a dark place at a temperature of 20 degrees C. for 16 hours and then in the light at a temperature of 30 degrees C. for 8 hours, which operation was repeated for ten days (hereinafter referred to as Condition 1). Then, it was observed with the naked eye whether the sprouted and grown seedlings were healthy or not.

The results are as seen in Table 2.

TABLE 2

| State of the Seedlings | |
|---|---|
| Seed | Percentage of Healthy Seedlings |
| Intact rice seeds | 64% |
| De-husked brown rice seeds | 78% |
| De-husked brown rice seeds processed with coating liquid A | 94% |

As seen above, the brown rice seeds which were de-husked and processed with coating liquid A, i.e., covered with a polyvinyl acetate binder, gave a larger number of healthy seedlings in Condition 1, compared to the intact rice seeds or the simply de-husked rice seeds.

EXAMPLE 1

Coating liquid B as indicated in the following Table 3 was sprayed on the de-husked rice seeds prepared as in Control Example 1 above, without washing the de-husked rice seeds with water or others, and dried to obtain the de-husked rice seeds coated with a polyvinyl acetate binder containing the insecticide, imidacloprid. The spray coating and drying were carried out as in Control Example 1 above.

The amount of coating liquid B used was 56 g per kg of the de-husked rice seeds. The quantities of imidacloprid and the polyvinyl acetate binder applied to the surface of the de-husked rice seeds were 5.6g and 4.8 g, respectively, per kg of the de-husked rice seeds.

TABLE 3

Coating Liquid B

| Component | Content, % by weight |
|---|---|
| Gaucho 70WS* | 14.3 |
| Polyvinyl acetate (binder) | 8.6 |
| Water | 77.1 |

*Gaucho 70WS, trademark, contains 70% by weight of imidacloprid.

Each 100 grains of the intact rice seeds, the de-husked rice seeds processed with coating liquid A and the de-husked rice seeds processed with coating liquid B were each sown on soil in a pot. Under this aerobic condition, they were kept in a dark place at a temperature of 30 degrees C. for 3 days and then in the light at a temperature of 20 degrees C. for 10 days (hereinafter referred to as Condition 2). Then, for possible phytotoxicity caused by imidacloprid, it was observed with the naked eye whether the sprouted and grown seedlings were healthy or not.

The results are as seen in Table 4.

TABLE 4

State of the Seedlings

| Seed | Percentage of Healthy Seedlings |
|---|---|
| Intact rice seeds | 77% |
| De-husked brown rice seeds processed with coating liquid A | 75% |
| De-husked brown rice seeds processed with coating liquid B | 75% |

As seen above, the rate of the healthy seedlings from the de-husked brown rice seeds processed with coating liquid A sprouted in Condition 2 is less than that in Condition 1, but is almost same as that of the intact seeds in Condition 2. In Condition 2, the rate of the healthy seedlings from the de-husked brown rice seeds processed with coating liquid B is same as that from the de-husked brown rice seeds processed with coating liquid A, which means that there is almost no phytotoxicity by imidacloprid and good sprouting comparable to intact seeds are attained.

EXAMPLE 2

Intact rice seeds, AKITAKOMACHI, were processed by twin rolls, MX-300 Pearlmate, (trademark, ex Iseki & Co., Ltd.) to remove the husk.

Coating liquid C as indicated in the following Table 5 was sprayed on the de-husked rice seeds prepared above, without washing the de-husked rice seeds with water or others, and dried to obtain the de-husked rice seeds coated with a binder. The spray coating and the drying were carried out as in Control Example 1 above.

The amount of coating liquid C used was 69 g per kg of the de-husked rice seeds. The quantities of pefurazoate (bactericidal agent), imidacloprid (insecticide) and the polyvinyl acetate binder applied to the surface of the de-husked rice seeds were 0.2 g, 11.2 g and 4.8 g, respectively, per kg of the de-husked rice seeds.

TABLE 5

Coating Liquid C

| Component | Content, % by weight |
|---|---|
| Healthied 20* | 1.4 |
| Gaucho 70WS** | 23.2 |
| Polyvinyl acetate (binder) | 7.0 |
| Water | 68.4 |

*Healthied 20, trademark, contains 20% by weight of pefurazoate.
**Gaucho 70WS, trademark, contains 70% by weight of imidacloprid.

Each 100 grains of the intact rice seeds, the de-husked rice seeds, the de-husked rice seeds processed with coating liquid A and the de-husked rice seeds processed with coating liquid C were sown on each filter paper (ex Schleicher & Schuel) which were folded into 50 folds in a plastic container and wetted with 60 cc of water. Under this aerobic condition, they were kept in a dark place at a temperature of 20 degrees C. for 16 hours and then in the light at a temperature of 30 degrees C. for 8 hours, which operation was repeated for seven days (hereinafter referred to as Condition 3). Then, it was observed with the naked eye whether the sprouted and grown seedlings were healthy or not.

The results are as seen in Table 6.

TABLE 6

State of the Seedlings

| Seed | Percentage of Healthy Seedlings |
|---|---|
| Intact rice seeds | 78% |
| De-husked brown rice seeds | 89% |
| De-husked brown rice seeds processed with coating liquid A | 95% |
| De-husked brown rice seeds processed with coating liquid C | 95% |

In Condition 3 here, the operation was repeated for 7 days, instead of 10 days in Condition 1. AKITAKOMACHI rice seeds were used here. The brown rice seeds which were de-husked and processed with coating liquid A, i.e., covered with a polyvinyl acetate binder, gave a larger number of healthy seedlings in Condition 3, compared to the intact rice seeds or the simply de-husked rice seeds. These results are same as those in the experiments in Condition 1. The rate of the healthy seedlings from the de-husked brown rice seeds processed with coating liquid C, i.e., covered with the polyvinyl acetate binder, bactericide pefurazoate and insecticide imidacloprid, is larger than those from the intact rice seeds and from the de-husked rice seeds, and almost same as that from the de-husked brown rice seeds processed with coating liquid A. Thus, good sprouting was attained without phytotoxicity.

EXAMPLE 3

Example 2 was repeated with the exception that the following coating liquid D was used.

The amount of coating liquid D used was 69 g per kg of the de-husked rice seeds. The quantities of pefurazoate (bactericidal agent), imidacloprid (insecticide) and the polyvinyl acetate binder applied to the surface of the de-husked rice seeds were 0.2 g, 11.2 g and 2.0 g, respectively, per kg of the de-husked rice seeds.

TABLE 7

| Coating Liquid D | |
| --- | --- |
| Component | Content, % by weight |
| Healthied 20* | 1.4 |
| Gaucho 70WS** | 23.0 |
| Polyvinyl pyrrolidone (binder) | 2.9 |
| Water | 72.5 |

*Healthied 20, trademark, contains 20% by weight of perurazoate.
**Gaucho 70WS, trademark, contains 70% by weight of imidacloprid.

The state of sprouting was observed in Condition 3 as in Example 2. Then, it was observed with the naked eye whether the sprouted and grown seedlings were healthy or not.

The results are as seen in Table 8.

TABLE 8

| State of the Seedlings | |
| --- | --- |
| Seed | Percentage of Healthy Seedlings |
| De-husked brown rice seeds processed with coating liquid D | 96% |

The rate of the healthy seedlings from the de-husked brown rice seeds processed with coating liquid D, i.e., covered with the polyvinyl pyrrolidone binder, bactericide pefurazoate and insecticide imidacloprid, is larger than those from the intact rice seeds and from the de-husked rice seeds, and almost same as that from the de-husked brown rice seeds processed with coating liquid A. Thus, good sprouting was attained without phytotoxicity.

EXAMPLE 4

Coating liquid E as indicated in the following Table 9 was sprayed on the de-husked rice seeds prepared as in Control Example 1 above, without washing the de-husked rice seeds with water or others, and dried to obtain the de-husked rice seeds coated with a polyvinyl pyrrolidone binder containing a bactericide, fludioxonil. The spray coating and the drying were carried out as in Control Example 1 above.

The amount of coating liquid E used was 41 g per kg of the de-husked rice seeds. The quantities of fludioxonil and the polyvinyl pyrrolidone binder applied to the surface of the de-husked nice seeds were 0.2 g and 2 g, respectively, per kg of the de-husked rice seeds.

TABLE 9

| Coating Liquid E | |
| --- | --- |
| Component | Content, % by weight |
| Savior* | 2.4 |
| Polyvinyl pyrrolidone (binder) | 4.9 |
| Water | 92.7 |

*Savior, trademark, contains 20% by weight of fludioxonil.

Each 100 grains of the de-husked rice seeds and the de-husked rice seeds processed with coating liquid E were sprouted and grown in Condition 1. Then, it was observed with the naked eye whether the sprouted and grown seedlings were healthy or not.

The results are as seen in Table 10.

TABLE 10

| State of the Seedlings | |
| --- | --- |
| Seed | Percentage of Healthy Seedlings |
| De-husked brown rice seeds | 78% |
| De-husked brown rice seeds processed with coating liquid E | 91% |

As seen above, the rate of the healthy seedlings from the de-husked brown rice seeds processed with coating liquid E is larger than that from the de-husked rice seeds, which means that there is almost no phytotoxicity by fludioxonil and better sprouting than that from the de-husked rice seeds is attained.

EXAMPLE 5

Example 4 was repeated with the exception that coating liquid F indicated in the following coating Table 11 was used.

The amount of coating liquid F used was 48.85 g per kg of the de-husked rice seeds. The quantities of fludioxonil (bactericidal agent), thiametoxam (insecticide) and a polyvinyl pyrrolidone binder applied to the surface of the de-husked rice seeds were 0.2 g, 5.5 g and 2.0 g, respectively, per kg of the de-husked rice seeds.

TABLE 11

| Coating Liquid F | |
| --- | --- |
| Component | Content, % by weight |
| Savior* | 2.0 |
| Cruiser** | 16.1 |
| Polyvinyl pyrrolidone (binder) | 4.1 |
| Water | 77.8 |

*Savior, trademark, contains 20% by weight of fludioxonil.
**Cruiser, trademark, contains 70% by weight of thiametoxam.

The state of sprouting was investigated as in Example 4. Thus, it was observed with the naked eye whether the sprouted and grown seedlings were healthy or not.

The results are as seen in Table 12.

TABLE 12

State of the Seedlings

| Seed | Percentage of Healthy Seedlings |
|---|---|
| De-husked brown rice seeds processed with coating liquid F | 88% |

The rate of the healthy seedlings from the de-husked brown rice seeds processed with coating liquid F, i.e., covered with the polyvinyl pyrrolidone binder, bactericide fludioxonil and insecticide thiametoxam, is larger than that from the de-husked rice seeds, which means that there is almost no phytotoxicity by fludioxonil or by thiametoxam and better sprouting than that from the de-husked rice seeds is attained.

EXAMPLE 6

The rice seeds as prepared in Examples 4 and 5 and the de-husked seeds were subjected to the following germination tests.

150 Milliliters of soil (particulate soil for cultivation, produced by Kumiai, sold by JA) were put in a tray of 200 ml. Each 100 grains of the aforesaid seeds were sown in each tray and covered with 20 ml of the aforesaid soil, to which 50 ml of water was then added. Under this aerobic condition, they were kept in a dark place at a temperature of 30 degrees C. for 3 days and then in the light at a temperature of 20 degrees C. for 7 days to be germinated. Then, growth of the seedlings and formation of mold were observed with the naked eye.

The results are as seen in Table 13.

TABLE 13

State of the Seedlings

| Seed | Formation of Mold | Growth of the Seedling |
|---|---|---|
| De-husked brown rice seeds | Remarkable | Usual |
| Seeds prepared in Example 4 | No | Good |
| Seeds prepared in Example 5 | No | Good |

Next, the rice seeds coated each with coating liquids A through F as in Control Example 1 and Examples 1 through 5 were cultivated according to a conventional manner where neither insecticide nor bactericide was sprinkled. As a result, the rice seeds coated with coating liquids B through F showed good growth, but the rice seeds coated with coating liquid A, i.e., coated by a binder alone showed severe damages by insects and diseases and the growth was impeded.

EXAMPLE 7 and COMPARISON EXAMPLE 1

In Example 7, coating liquid G as indicated in the following Table 14 was sprayed on the de-husked rice seeds prepared as in Control Example 1 above, without washing the de-husked rice seeds with water or others, and dried to obtain the de-husked rice seeds coated with a polyvinyl alcohol binder containing the bactericide, fludioxonil.

The amount of coating liquid G used was 41 g per kg of the de-husked rice seeds. The quantities of fludioxonil and the polyvinyl alcohol binder applied to the surface of the de-husked rice seeds were 0.2 g and 2 g, respectively, per kg of the de-husked rice seeds.

TABLE 14

Coating Liquid G

| Component | Content, % by weight |
|---|---|
| Savior* | 2.4 |
| Polyvinyl alcohol (binder) | 4.9 |
| Water | 92.7 |

*Savior, trademark, contains 20% by weight of fludioxonil.

Meanwhile in Comparison Example 1, the de-husked rice seeds as prepared in Control Example 1 were washed with flowing tap water for 2 hours. Coating liquid H consisting of 5% by weight of the polyvinyl alcohol binder and 95% by weight of water was sprayed on the rice seeds, and dried to obtain the de-husked rice seeds coated with a polyvinyl alcohol binder alone. The amount of coating liquid H used was 40 g per kg of the de-husked rice seeds. The quantity of the polyvinyl alcohol binder applied to the surface of the de-husked rice seeds was 2 g, per kg of the de-husked rice seeds.

Both in Example 7 and Comparison Example 1, the spray coating and the drying were carried out as in Control Example 1.

Each 100 grains of the intact rice seeds, the de-husked rice seeds and the two types of the de-husked rice seeds processed above were sown on soil in each pot. Under this aerobic condition, they were kept in a dark place at a temperature of 20 degrees C. for 16 hours and then in the light at a temperature of 30 degrees C. for 8 hours, which operations was repeated for 8 days (hereinafter referred to as Condition 4). Then, growth of the seedlings and formation of mold were observed with the naked eye.

The results are as seen in Table 14.

TABLE 14

State of the Seedlings

| Seed | Formation of Mold | Growth of the Seedling |
|---|---|---|
| Intact rice seeds | No | Good |
| De-husked brown rice seeds | A little | Very good |
| Seeds prepared in Example 7 | No | Very good |
| Seeds prepared in Com. Example 1 | Remarkable | Good |

In Example 7 where the rice seeds were coated with the polyvinyl alcohol containing the bactericide, the growth of the seedlings was very good and no formation of mold was observed at all. Meanwhile, in Comparison Example 1, which follows Japanese Patent No. 2,866,921, the growth of the seedlings was poorer than that in Example 7 and the formation of mold was remarkable, which apparently adversely affects the growth of the seedlings in future development.

It is believed that a reason why mold occurs remarkably in Comparison Example 1 is that removal of husk causes fine flaws on the surface of the seeds; the flaws are enlarged by the water washing for asepsis; a lot of saccharides come out through the enlarged flaws, which are utilized by mold for proliferation. In contrast, in Example 7, no water washing take place and, therefore, no enlargement of flaws take place.

EXAMPLE 8

Coating liquids I, J and K as indicated in the following Tables 15, 16 and 17 were each sprayed on the de-husked rice seeds prepared as in Control Example 1 above, without washing the de-husked rice seeds with water or others, and dried to obtain three types of the de-husked rice seeds coated with a polyvinyl alcohol with different amounts of polyurethane, containing an insecticide, imidacloprid. The spray coating and the drying were carried out as in Control Example 1 above.

The amounts of coating liquids I, J and K used was each 47.77 g per kg of the de-husked rice seeds. The quantity of imidacloprid applied to the surface of the de-husked rice seeds was always 5.5 g per kg of the de-husked rice seeds. The quantity of the binder is 3.92 g of the polyvinyl alcohol and 0 g of the polyurethane with coating liquid I; 3.53 g of the polyvinyl alcohol and 0.39 g of the polyurethane with coating liquid J; and 2.94 g of the polyvinyl alcohol and 0.98 g of the polyurethane with coating liquid K, per kg of the de-husked rice seeds.

TABLE 15

Coating Liquid I

| Component | Content, % by weight |
|---|---|
| Gaucho 70WS* | 16.4 |
| Polyvinyl alcohol (binder) | 8.2 |
| Polyurethane (binder) | 0 |
| Water | 75.4 |

*Gaucho 70WS, trademark, contains 70% by weight of imidacloprid.

TABLE 16

Coating Liquid J

| Component | Content, % by weight |
|---|---|
| Gaucho 70WS* | 16.4 |
| Polyvinyl alcohol (binder) | 7.4 |
| Polyurethane (binder) | 0.8 |
| Water | 75.4 |

TABLE 17

Coating Liquid K

| Component | Content, % by weight |
|---|---|
| Gaucho 70WS* | 16.4 |
| Polyvinyl alcohol (binder) | 6.2 |
| Polyurethane (binder) | 2.0 |
| Water | 75.4 |

Each 5 g of the de-husked rice seeds thus processed with coating liquid I, J or K were placed on each petri-dish, to which 10 ml of water were poured. After a predetermined period of time at room temperature, a concentration of imidacloprid in the water was determined by liquid chromatography.

The results are as seen in Table 18.

TABLE 18

| | Released amount of imidacloprid, by weight* Type of the coating liquid | | |
|---|---|---|---|
| Time, hour | I | J | K |
| 1 | 8.8 | 2.7 | 1.9 |
| 2 | 11.4 | 4.3 | 3.5 |
| 4 | 15.7 | 7.3 | 5.9 |
| 6 | 21.1 | 10.0 | 8.1 |
| 24 | 38.0 | 29.4 | 28.0 |

*The released amount of imidacloprid is indicated as a ratio of it to the weight of imidacloprid contained in the rice seeds.

It is seen from the above results that when polyurethane is used in addition to polyvinyl alcohol, a releasing rate of imidacloprid into water is decreased. That is, the released amount in the case of the rice seeds processed with coating liquid K containing polyurethane is 8.1% by weight at 6 th hour, while that in the case of the rice seeds processed with coating liquid I containing no polyurethane is 8.8% by weight already at 1st hour.

The invention claimed is:

1. A rice seed coated with an agricultural chemical, comprising a rice seed deprived of husk and the surface of said rice seed being coated with a binder containing an agricultural chemical to protect said seed from insects and disease; wherein said coated rice seed is not washed after de-husking; and, wherein said coated rice seed develops a radicle first before a coleoptile when germinated in aerobic conditions.

2. The rice seed as claimed in claim 1, wherein said rice seed is selected from the group consisting of *Oryza sativa* sp. *japonica, Oryza sativa* sp. *javanica Oryza sativa* sp. *indica, and hybrids* thereof.

3. The rice seed as claimed in claim 1, wherein said agricultural chemical is selected from the group consisting of fungicidal agents, bactericidal agents and insecticidal agents.

4. The rice seed as claimed in claim 3, wherein a fungicidal or bactericidal agent is applied in an amount of 0.1 to 10 g per kg of the de-husked rice.

5. The rice seed as claimed in claim 3, wherein an insecticidal agent is applied in an amount of 3 to 20 g per kg of the de-husked rice.

6. The rice seed as claimed in claim 3, wherein the fungicide is selected from the group consisting of phenylpyrrole fungicides, azole fungicides, and strobilurine fungicides.

7. The rice seed as claimed in claim 3, wherein the insecticide is selected from the group consisting of neonicotinoid insecticides, carbamate insecticides, pyrethroid ether insecticides, and pyridine azomethine insecticides.

8. The rice seed as claimed in claim 1, wherein the binder is selected from the group consisting of polyvinyl acetates, polyvinyl alcohols, and polyvinyl pyrrolidones.

9. The rice seed as claimed in claim 1, wherein the binder is a mixture of 0 to 50% by weight of polyurethane and 100 to 50% by weight of polyvinyl alcohol.

10. A method of germinating said seeds as claimed in claim 1, wherein said seeds are kept for at least three days at 20° C. to 40° C. in aerobic conditions thereby lending to emergence of a radicle first before emergence of a coleoptile.

11. A method according to claim 10, wherein said seeds are kept for 4 to 9 days at 25° C. to 35° C.

12. A method according to claim 10, wherein said seeds are maintained at around 30° C.

* * * * *